US010952705B2

(12) United States Patent
Sudhakar et al.

(10) Patent No.: US 10,952,705 B2
(45) Date of Patent: Mar. 23, 2021

(54) METHOD AND SYSTEM FOR CREATING AND UTILIZING A PATIENT-SPECIFIC ORGAN MODEL FROM ULTRASOUND IMAGE DATA

(71) Applicant: GENERAL ELECTRIC COMPANY, Schenectady, NY (US)

(72) Inventors: Prasad Sudhakar, Karnataka (IN); Justin Daniel Lanning, Wauwatosa, WI (US); Pavan Kumar Annangi, Karnataka (IN); Michael Washburn, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 627 days.

(21) Appl. No.: 15/860,771

(22) Filed: Jan. 3, 2018

(65) Prior Publication Data

US 2019/0200964 A1    Jul. 4, 2019

(51) Int. Cl.
*A61B 8/08* (2006.01)
*A61B 8/00* (2006.01)
*G06T 7/00* (2017.01)

(52) U.S. Cl.
CPC ............ *A61B 8/5246* (2013.01); *A61B 8/085* (2013.01); *A61B 8/0833* (2013.01);
(Continued)

(58) Field of Classification Search
CPC ..... A61B 8/0833; A61B 8/085; A61B 8/4245; A61B 8/4254; A61B 8/4488; A61B 8/461;
(Continued)

(56) References Cited

U.S. PATENT DOCUMENTS 8,681,152 B2    3/2014 Kubota et al.
8,812,431 B2    8/2014 Voigt et al.
(Continued)

OTHER PUBLICATIONS

Myronenko, Andriy and Song, Xubo, "Point Set Registration: Coherent Point Drift," Department of Science and Engineering, School of Medicine, Oregon Health and Science University, arXiv:0905.2635v1 [cs.CV] May 15, 2009, pp. 1-14, Portland, OR.
(Continued)

*Primary Examiner* — Amelie R Davis
(74) *Attorney, Agent, or Firm* — McAndrews, Held & Malloy, Ltd.; Jacob Groethe; David Bates

(57) ABSTRACT

A system and method for generating a patient-specific organ model is provided. The method may include receiving ultrasound images of an organ and probe position data corresponding with each of the ultrasound images. The method may include receiving identification of landmarks in the ultrasound images corresponding with pre-defined landmarks of a generic geometric organ model. The method may include automatically identifying surface points of the organ in the ultrasound images. The method may include generating a patient-specific ultrasound point cloud of the organ based on the received identification of the landmarks, the automatically identified surface points of the organ, and the probe position data. The method may include registering a point cloud of the generic geometric model to the patient-specific ultrasound point cloud to create a patient-specific organ model. The method may include presenting the patient-specific organ model at a display system.

20 Claims, 10 Drawing Sheets

(52) U.S. Cl.
CPC .......... *A61B 8/4245* (2013.01); *A61B 8/4254* (2013.01); *A61B 8/4488* (2013.01); *A61B 8/461* (2013.01); *A61B 8/5207* (2013.01); *A61B 8/5223* (2013.01); *G06T 7/0014* (2013.01); *G06T 2207/10028* (2013.01); *G06T 2207/10136* (2013.01); *G06T 2207/20081* (2013.01); *G06T 2207/20101* (2013.01); *G06T 2207/30096* (2013.01); *G06T 2207/30204* (2013.01)

(58) Field of Classification Search
CPC ... A61B 8/5207; A61B 8/5223; A61B 8/5246; G06T 2207/10028; G06T 2207/10132; G06T 2207/10136; G06T 2207/20081; G06T 2207/20101; G06T 2207/30056; G06T 2207/30096; G06T 2207/30204; G06T 7/0014; G06T 7/12; G06T 7/149
See application file for complete search history.

(56) References Cited

U.S. PATENT DOCUMENTS

| | | |
|---|---|---|
| 9,092,666 B2 | 7/2015 | Kang et al. |
| 9,336,592 B2 | 5/2016 | Fan et al. |
| 9,514,280 B2 | 12/2016 | Kang et al. |
| 2008/0240337 A1 | 10/2008 | Galant et al. |
| 2012/0027277 A1 | 2/2012 | Vik et al. |
| 2013/0297265 A1* | 11/2013 | Baloch ................ A61B 34/10 703/1 |
| 2014/0221825 A1* | 8/2014 | Mahfouz ............... G06T 7/564 600/424 |
| 2016/0364880 A1* | 12/2016 | Barratt ................. G06T 7/344 |
| 2017/0312032 A1* | 11/2017 | Amanatullah ......... G09B 23/30 |
| 2018/0182096 A1* | 6/2018 | Grady ................. G16H 50/50 |
| 2019/0290247 A1* | 9/2019 | Popovic ............. A61B 1/00009 |

OTHER PUBLICATIONS

Hu, Yipeng, et al., "Deformable Vessel-Based Registration Using Landmark-Guided Coherent Point Drift," Springer-Verlag Berlin Heidelberg 2010, vol. 6326, pp. 60-69.

Ronneberger, Olaf, et al., "U-Net: Convoluational Networks for Biomedical Image Segmentation," WWW.http://imb.informatik.uni-freiburg.de/, arXiv:1505.04597v1 [cs.CV] May 18, 2015, pp. 1-8.

Yang, Jimei, et al., "Object Contour Detection with a Fully Convolutional Encoder-Decoder Network," arXiv:1603.04530v1 [cs.CV] May 15, 2016, pp. 1-10.

* cited by examiner

METHOD AND SYSTEM FOR CREATING AND UTILIZING A PATIENT-SPECIFIC ORGAN MODEL FROM ULTRASOUND IMAGE DATA

FIELD

Certain embodiments relate to ultrasound imaging. More specifically, certain embodiments relate to a method and system for generating a patient-specific organ model from ultrasound image data. The patient-specific organ model may be utilized in ultrasound-guided procedures, follow-up studies, and/or to otherwise provide a three-dimensional context to a set of two-dimensional ultrasound images.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Traditionally, documentation of ultrasound examinations has been limited to still image snapshots of representative structures. These still image snapshots typically have limited value for re-evaluating an examination or comparing with older examinations. Still images also make it difficult to determine whether a lesion has appeared since a previous examination. Instead, doctors may be left to rely on whether the lesion was mentioned in the previous report. Such low levels of confidence are incompatible with the demands of diagnostic imaging modalities.

Due to some of the difficulties associated with ultrasound imaging, other imaging modalities such as computed tomography (CT) and magnetic resonance (MR) imaging modalities may be used to perform various examinations, such as liver volume measurements and studies tracking disease progression over time. CT and MR imaging modalities, however, are more expensive and invasive than ultrasound imaging. For example, CT examinations expose patients to radiation and both CT and MR examinations may use a contrast injection that may be harmful to patients with renal challenges.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for generating a patient-specific organ model from ultrasound image data, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
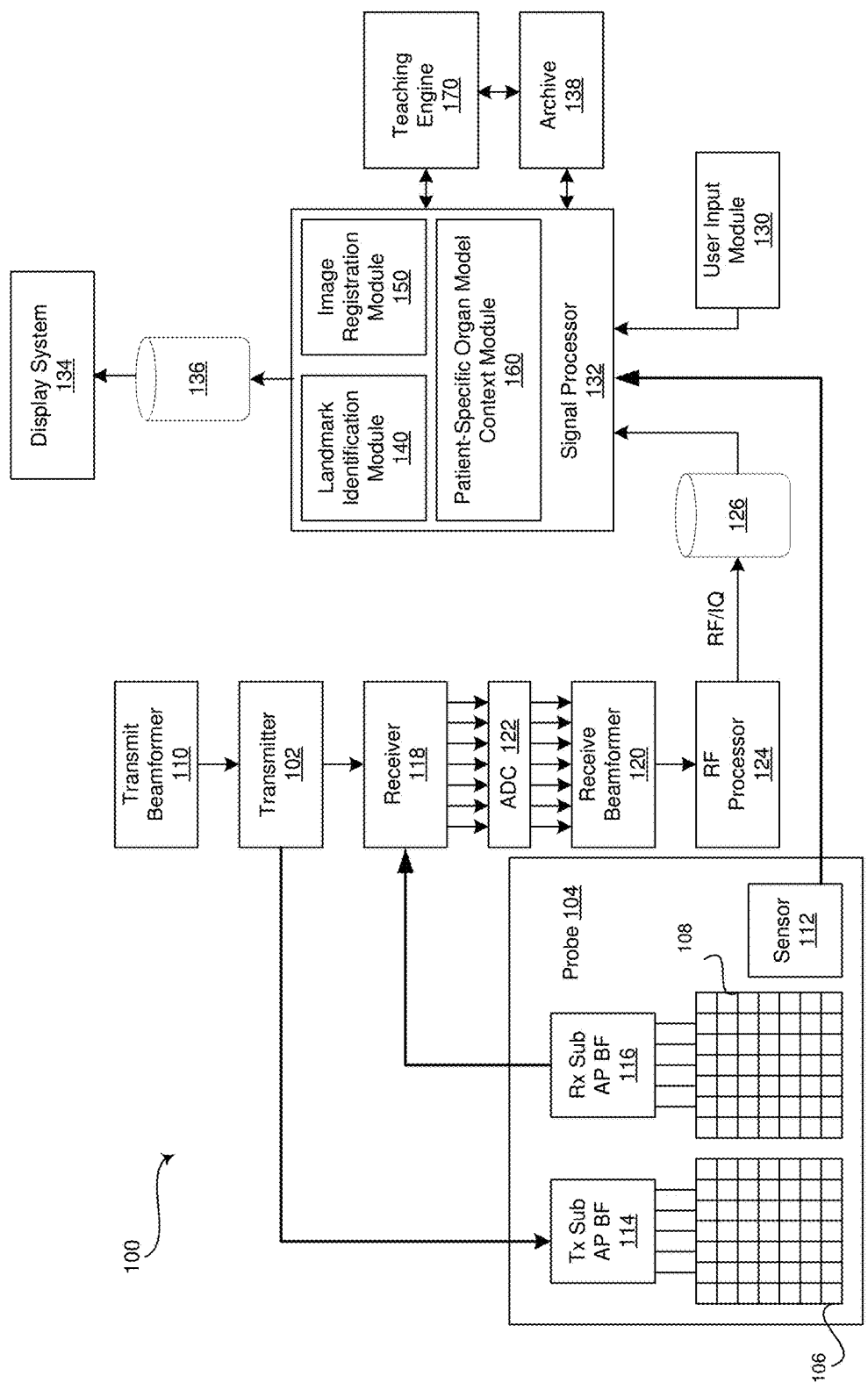
FIG. 1 is a block diagram of an exemplary ultrasound system that is operable to generate a patient-specific organ model from ultrasound image data, in accordance with various embodiments.

Certain embodiments may be found in a method and system for generating a patient-specific organ model from ultrasound image data. Various embodiments have the technical effect of providing a three-dimensional context for an associated set of two-dimensional ultrasound image data. The three-dimensional context may include contextual markers illustrating where in a patient-specific organ model a two-dimensional image being viewed is located and/or where in the patient-specific organ model marked structures such as lesions may be found. Moreover, certain embodiments have the technical effect of providing a patient specific model that may be associated with current and/or subsequent two-dimensional ultrasound image data sets based on probe position sensor data associated with the acquired two-dimensional ultrasound image data. Furthermore, various embodiments have the technical effect of providing assistance with real-time navigation of ultrasound-guided procedures by illustrating the probe position with respect to the organ surface and lesion locations illustrated by a patient-specific organ model. Aspects of the present disclosure have the technical effect of providing a patient-specific organ model enabling volume measurements and/or for measuring growth over time.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as three-dimensional (3D) mode, B-mode, CF-mode, and/or sub-modes of B-mode and/or CF such as Shear Wave Elasticity Imaging (SWEI), TVI, Angio, B-flow, BMI, BMI Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to generate a patient-specific organ model 700 from ultrasound image data, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, a display system 134, an archive 138, and a teaching engine 170.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. The ultrasound system 100 may include a position sensing system 112 attached to the probe 104. The position sensing system 112 may include an optical tracking system, magnetic position system, a sensor in a probe holder, a motion sensing system, and/or any suitable system or combinations of systems configured to detect the position of the probe 104. For example, the ultrasound system 100 may include an external magnetic field generator comprising a coil and/or a permanent magnet that when energized, may generate a static external magnetic field. The position sensing system 112 may be configured to detect a preexisting magnetic field or the magnetic field generated by the external magnetic field generator. The external magnetic field generator may be configured to generate a magnetic field with a gradient sot that the position of the magnetic position sensor may be determined based on the detected magnetic field. In various embodiments, the position sensing system 112 may provide the probe position data to the signal processor 132 of the ultrasound system 100 for association with ultrasound image data acquired by the ultrasound probe 104 at the corresponding probe positions. In certain embodiment, the ultrasound probe 104 may be operable to acquire ultrasound image data covering at least a substantial portion of an organ, such as the liver or any suitable organ.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the disclosure is not limited in this regard. Accordingly, in some embodiments, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, scan parameters, settings, select protocols and/or templates, identify landmarks in ultrasound image data, navigate two-dimensional image viewing using a three-dimensional patient-specific organ model, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the position sensing system 112, the receiver 118, the receive beamformer 120, the RF processor 124, the RF/IQ buffer 126, the user input module 130, the signal processor 132, the image buffer 136, the display system 134, the archive 138, and/or the teaching engine 170. The user input module 130 may include button(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display. In various embodiments, landmarks in two-dimensional ultrasound image data that correspond to pre-defined landmarks in a generic geometric organ model may be selected in response to a directive received via the user input module 130. In certain embodiments, a two-dimensional ultrasound image data set may be navigated in response to a directive received via the user input module 130 to select positions within a three-dimensional patient-specific organ model associated with the two-dimensional ultrasound image data set.

The signal processor 132 may comprise suitable logic, circuitry, interfaces and/or code that may be operable to process ultrasound scan data (i.e., RF signal data or IQ data pairs) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, each of the ultrasound images generated by the signal processor 132 may be associated with probe position data received from the probe position sensing system 112 of the ultrasound probe 104 to associate each of the ultrasound images with the position of the probe at the time of ultrasound image data acquisition. The processed image data and associated probe position data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise a landmark identification module 140, an image registration module 150, and a patient-specific organ model context module 160.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

Figure 2:
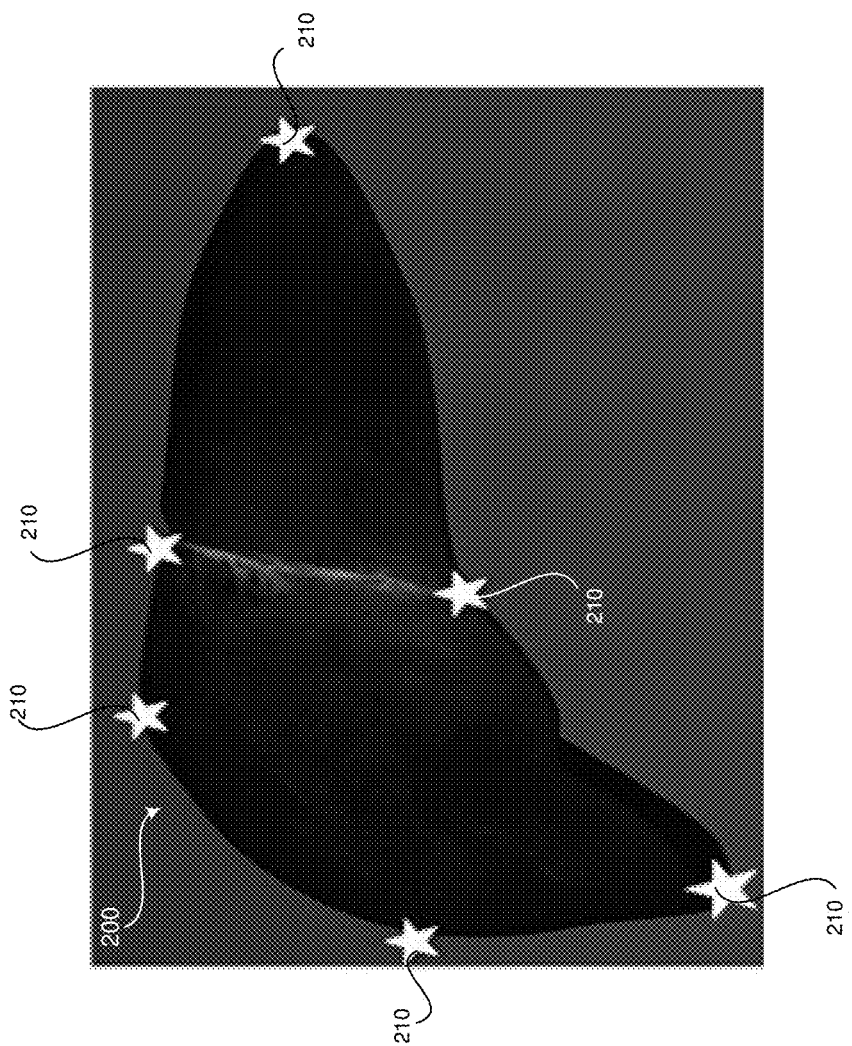
FIG. 2 is a perspective view of an exemplary generic geometric organ model having pre-defined landmarks, in accordance with exemplary embodiments.

The signal processor 132 may include a landmark identification module 140 that comprises suitable logic, circuitry, interfaces and/or code that may be operable to receive identification of and/or automatically identify landmarks in acquired ultrasound image data. The landmarks 310, 510 may be associated with pre-defined landmarks 210, 410 in a generic geometric organ model 200, 400 and/or may be surface points 505 of an imaged organ 500. FIG. 2 is a perspective view of an exemplary generic geometric organ model 200 having pre-defined landmarks 210, in accordance with exemplary embodiments. Referring to FIG. 2, the generic geometric organ model 200 may include pre-defined landmarks 210 at, for example, midpoints and/or at one or more of the most inferior, superior, lateral, medial, anterior, and/or posterior points, among other points, on an organ. The organ may be a liver as shown in FIG. 2 or any suitable organ. For example, using the user input module 130, an ultrasound operator may manually identify landmark points 310, 510 in acquired ultrasound image data, corresponding with pre-defined landmarks 210, 410 in a generic geometric organ model 200, 400, as the ultrasound image data is being acquired by the operator via the ultrasound probe 104. As another example, a doctor may manually identify the landmark points 310, 510 in a stored ultrasound image data set.

Figure 3:
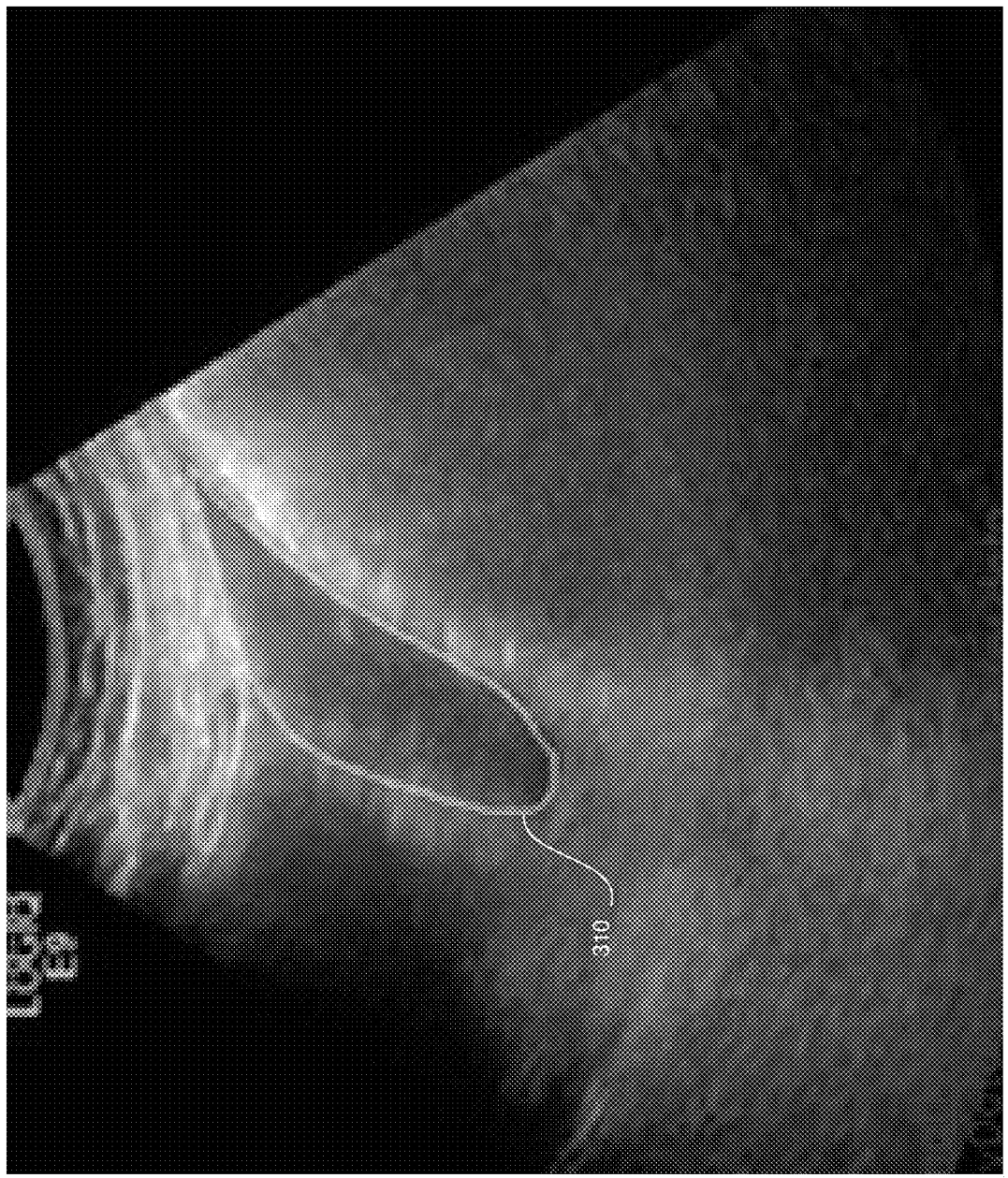
FIG. 3 is an exemplary ultrasound image illustrating an identified landmark in the ultrasound image data, in accordance with various embodiments.

FIG. 3 is an exemplary ultrasound image 300 illustrating an identified landmark 310 in the ultrasound image data 300, in accordance with various embodiments. Referring to FIG. 3, an ultrasound image 300 having ultrasound data corresponding with the structure of a portion of the liver is shown. The potion of the liver in the ultrasound image 300 is identified by marker 310. The identification marker 310 may be added via a user input module 130 to the ultrasound image 300 during image acquisition or when reviewing stored image data, for example. The identification marker 310 may correspond with a landmark 210, 410 of a generic geometric organ model 200, 400, such as the most lateral landmark in a generic geometric liver model.

Referring again to FIG. 1, the landmark identification module 140 may include image detection algorithms, one or more deep neural networks and/or may utilize any suitable form of image detection techniques or machine learning processing functionality configured to automatically identify landmarks in the ultrasound image data. For example, the landmark identification module 140 may be made up of an input layer, an output layer, and one or more hidden layers in between the input and output layers. Each of the layers may be made up of a plurality of processing nodes that may be referred to as neurons. For example, the input layer may have a neuron for each pixel or a group of pixels from the ultrasound images of the organ. The output layer may have a neuron corresponding to each structure of the organ being images. As an example, if imaging a liver, the output layer may include neurons for a diaphragm, gallbladder, inferior vena cava, middle, liver-fat boundary, liver surface points, unknown, and/or other. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks 310, 510 in the ultrasound image data 300. The processing performed by the landmark identification module 140 deep neural network may identify organ surface points with a high degree of probability.

Figure 5:
FIG. 5 is an exemplary patient-specific ultrasound point cloud having identified landmarks, in accordance with various embodiments.
Figure 6:
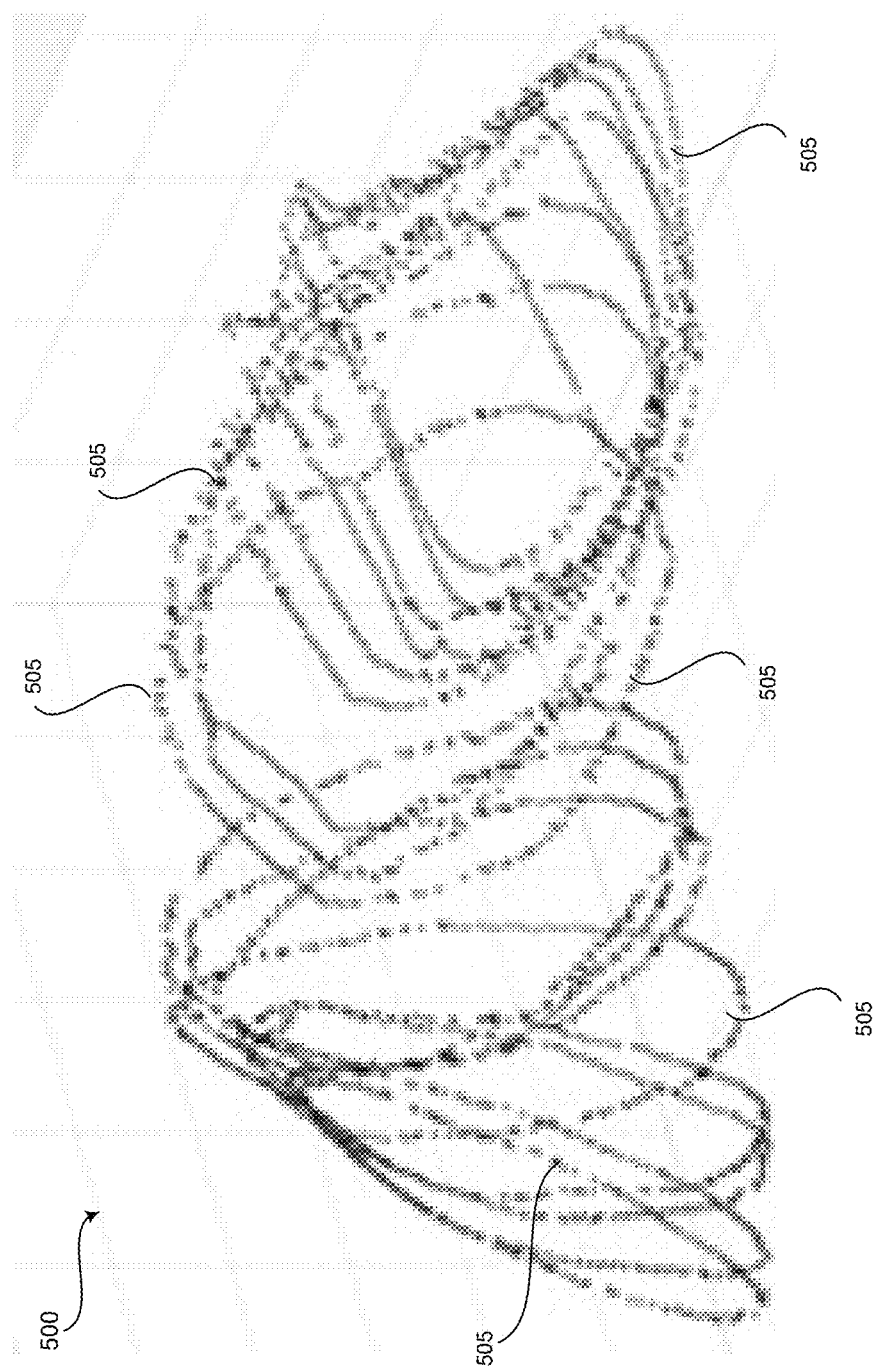
FIG. 6 is an exemplary patient-specific ultrasound point cloud, in accordance with exemplary embodiments.

In various embodiments, the landmark identification module 140 may comprise suitable logic, circuitry, interfaces and/or code that may be operable to generate a patient-specific ultrasound point cloud 500 made up of the landmarks 505, 510 received via the user input module 130 and/or automatically identified by the landmark identification module 140. The points 505, 510 of the patient-specific ultrasound point cloud 500 may be positioned based on the ultrasound probe position data received from the position sensing system 112. FIGS. 5 and 6 are exemplary patient-specific ultrasound point clouds 500, in accordance with various embodiments. Referring to FIGS. 5 and 6, the patient-specific ultrasound point clouds 500 may be formed by the landmark identification module 140 based on the user-identified landmarks 510, the automatically-identified surface points 505, and position data provided by the position sensing system 112 and associated with the ultrasound image data 300 from which the landmarks 310, 510 and surface points 505 are identified.

Figure 4:
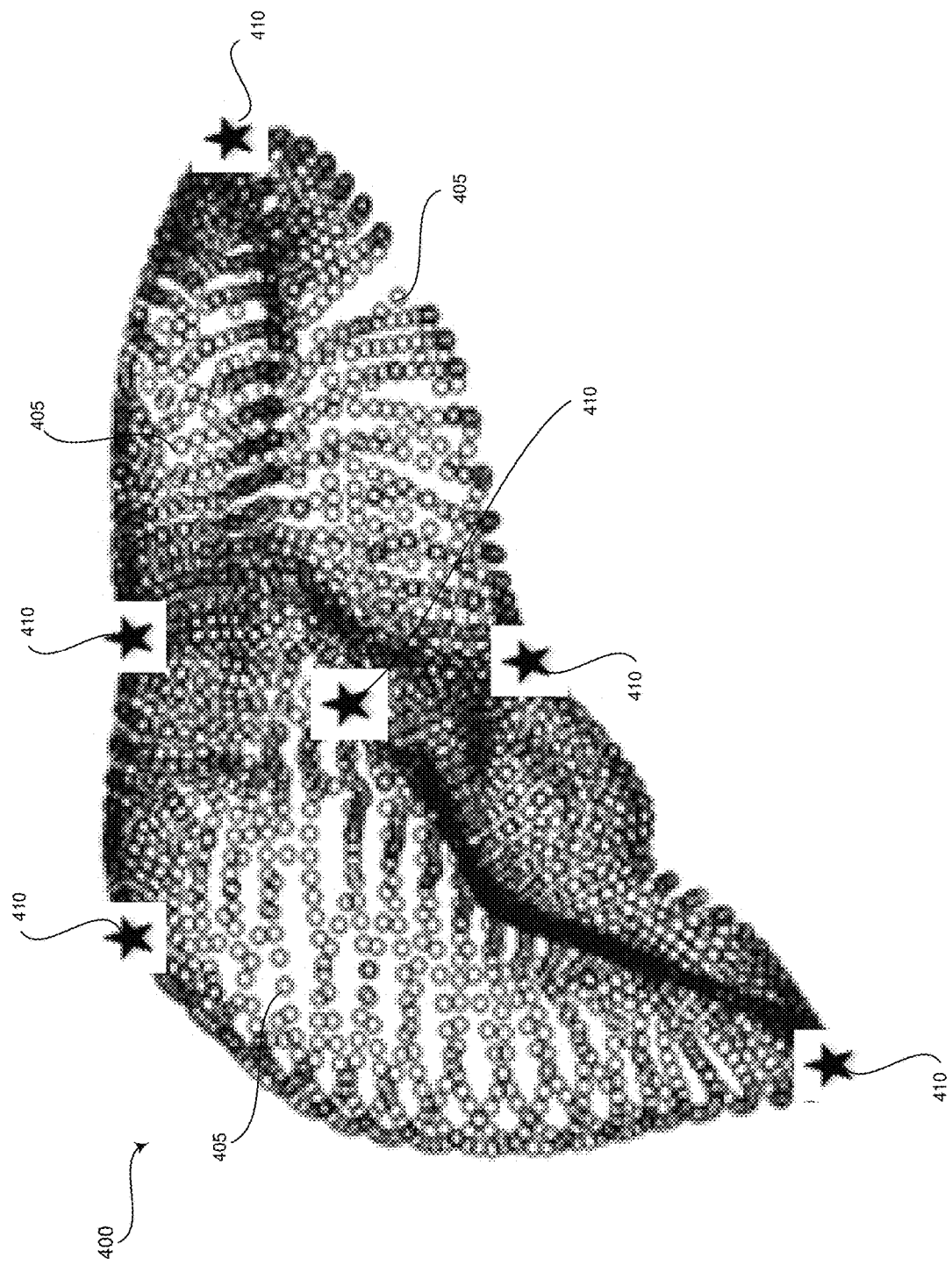
FIG. 4 is a perspective view of an exemplary generic geometric organ model point cloud with pre-defined landmarks corresponding to the generic geometric organ model having pre-defined landmarks of FIG. 2, in accordance with exemplary embodiments.
Figure 7:
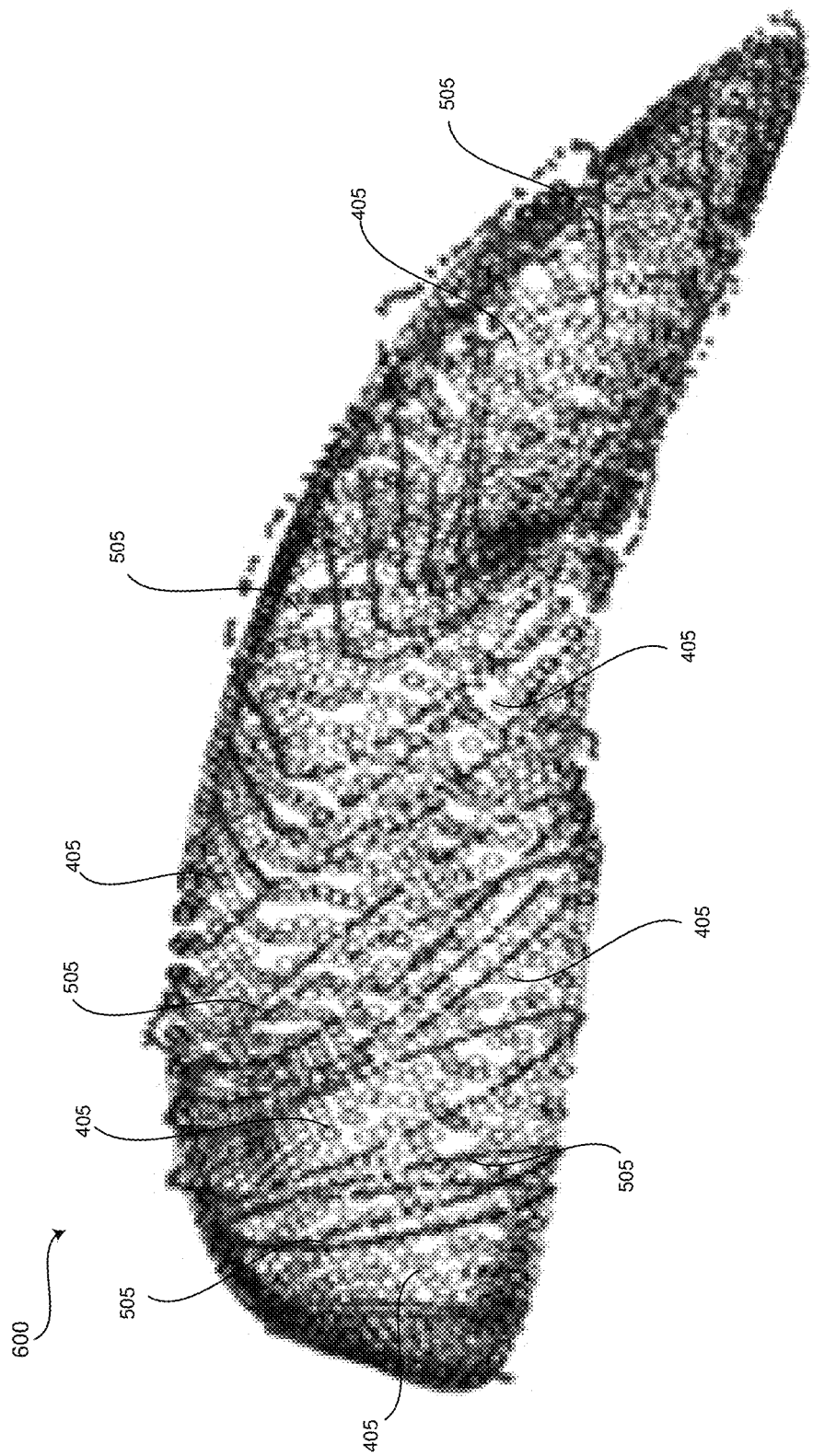
FIG. 7 is an exemplary generic geometric organ model point cloud registered with a patient-specific ultrasound point cloud, in accordance with various embodiments.

The signal processor 132 may include an image registration module 150 that comprises suitable logic, circuitry, interfaces and/or code that may be operable to register a point cloud 400 corresponding with the generic geometric organ model 200 to the patient-specific ultrasound point cloud 500 created with the landmarks 310, 510 and surface points 505 identified in the acquired ultrasound images 300. FIG. 4 is a perspective view of an exemplary generic geometric organ model point cloud 400 with pre-defined landmarks 410 corresponding to the generic geometric organ model 200 having pre-defined landmarks 210 of FIG. 2, in accordance with exemplary embodiments. Referring to FIG. 4, the generic geometric organ model point cloud 400 comprises surface points 405 and landmarks 410 corresponding with the surface of the generic geometric organ model 200 and the pre-defined landmarks 210, respectively. FIG. 7 is an exemplary generic geometric organ model point cloud 400 registered with a patient-specific ultrasound point cloud 500, in accordance with various embodiments. Referring to FIG. 7, the registered point clouds 600 may comprise the generic geometric organ model point cloud 400 surface points 405 and/or landmarks 410 deformed to align with the surface points 505 and/or landmarks 510 of the ultrasound point cloud 500. The landmarks 410 and/or surface points 405 of the generic geometric organ model point cloud 400 may be deformed to register with the ultrasound point cloud 500 landmarks 510 and/or surface points 505 using image registration techniques, such as landmark-guided coherent point drift (CPD) algorithms or any suitable image registration technique.

As an alternative to registering the generic geometric model point cloud 400 to the patient-specific ultrasound point cloud 500, the image registration module 150 may additionally and/or alternatively comprise suitable logic, circuitry, interfaces and/or code that may be operable to register a mesh model with detailed node connectivity details corresponding with the generic geometric organ model 200 to the landmarks 310, 510 and surface points 505 identified in the acquired ultrasound images 300. For example, iterative closest point registration or any suitable mesh registration method may be applied to deform the mesh model of the generic geometric organ model 200 to match the patient specific landmarks 310, 510 and surface points 505.

The image registration module 150 may comprise suitable logic, circuitry, interfaces and/or code that may be operable to create a patient-specific organ model 700 by converting the registered point clouds 600 and/or registered mesh model to the patient-specific organ model 700. For example, the image registration model 150 may generate the patient-specific organ model 700 by, among other things, providing surfaces joining the points of the registered point clouds 600 and post-processing the surfaces to provide smoothing, texturing, and the like. The image registration module 150 may link the ultrasound images used to create the patient-specific organ model 700 and/or subsequently acquired ultrasound images to the patient-specific organ model 700 based on the probe position data provided by the position sensing system 112 that is associated with acquired ultrasound images by the signal processor 132. Each of the positions within the patient-specific organ model 700 may correspond with one or more ultrasound images 300. The image registration module 150 may store the patient-specific organ model 700 in archive 138 or any suitable data storage medium.

The signal processor 132 may include a patient-specific organ model context module 160 that comprises suitable logic, circuitry, interfaces and/or code that may be operable to present the patient-specific organ model 700 at the display system 134. In an exemplary embodiment, the patient-specific organ model context module 160 may be used to measure the volume, length, width, depth, and any other suitable measurement of the patient-specific organ model 700. The measurements may be stored at archive 138 and/or at any suitable storage medium. The measurements may additionally and/or alternatively be presented at the display system 134. In a representative embodiment, the patient-specific organ model 700 may be used to perform real-time navigation of a biopsy or any suitable surgical procedure. For example, the patient-specific organ model context module 160 may overlay an icon representing the position of the needle or other surgical equipment on the patient-specific organ model 700. In certain embodiments, the patient-specific organ model 700 may include contextual markers 710 and/or may be selectable to navigate to an ultrasound image from an ultrasound image set that corresponds with the selected position in the patient-specific organ model 700. The contextual markers 710 may include markers for identifying the position of an ultrasound image 300 being presented with the patient-specific organ model 700 at the display system(s) 134. In various embodiments, the contextual markers 710 may include markers illustrating a position of identified structure, such as lesions that may have been marked in an ultrasound image 300 by an ultrasound operator or reviewing doctor, in the patient-specific organ model 700. In certain embodiments, the contextual markers 710 may include markers for identifying the position of a particular ultrasound image 300 having ultrasound operator and/or doctor notes with reference to the patient-specific organ model 700. In an exemplary embodiment, the contextual markers 710 may identify a current probe 104 location, key landmark points, or any suitable information. The contextual markers 710 may be color-coded to identify the meaning of the marker and/or the user that added the marker, among other things.

Figure 8:
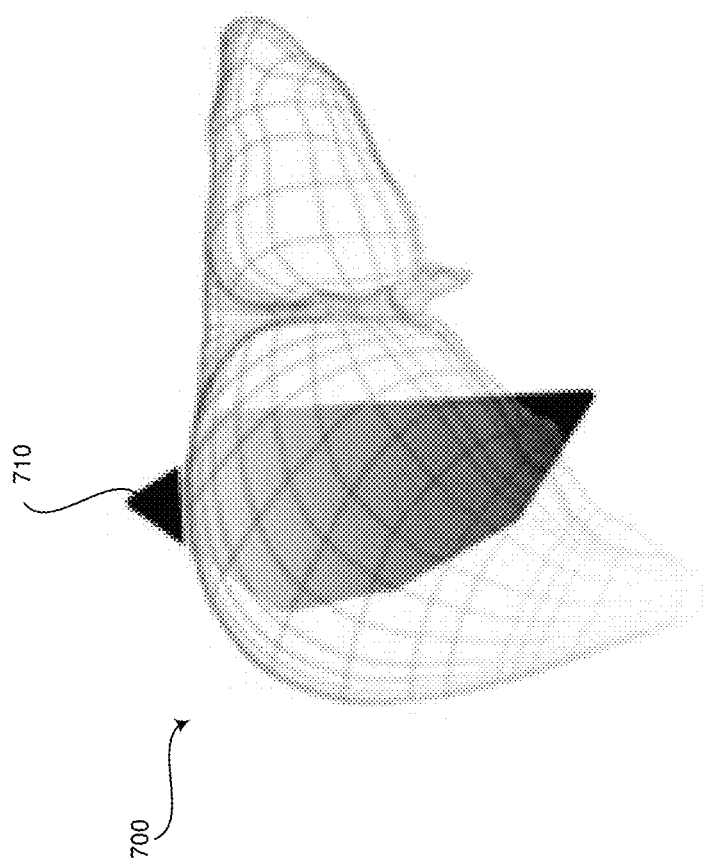
FIG. 8 is a perspective view of an exemplary patient-specific organ model having an exemplary contextual marker, in accordance with exemplary embodiments.

FIG. 8 is a perspective view of an exemplary patient-specific organ model 700 having an exemplary contextual marker 710, in accordance with exemplary embodiments. Referring to FIG. 8, the patient-specific organ model 700 comprises a contextual marker 710 that identifies the position of an ultrasound image 300 that, for example, is being displayed at the display system 134. The contextual marker 710 and its position with reference to the patient-specific organ model 700 provide a three-dimensional context to the two-dimensional ultrasound image 300 being presented. In various embodiments, positions within the patient-specific organ model 700 may be selected by the user input module 130 to navigate to different images in the ultrasound image set corresponding with the patient-specific organ model 700. The patient-specific organ model 700 may be presented at a same display of the display system 134 as the two-dimensional ultrasound image 300, a different display of the display system 134, at the user input module 130 such as on a touch pad, and/or at any suitable display medium.

In various embodiments, the portion of the patient-specific organ model 700 corresponding with the displayed two-dimensional ultrasound image 300 may be superimposed on the two-dimensional ultrasound image 300. In this way, a user may view the accuracy of the patient-specific organ model 700 with respect to the two-dimensional ultrasound image 300 based on the alignment of the portion of the model 700 with respect to the corresponding structure in the image 300. In certain embodiments, a user may fine tune the model by selecting additional landmarks in the two-dimensional ultrasound image 300 to more accurately align the patient-specific organ model 700 with the two-dimensional image 300.

Figure 9:
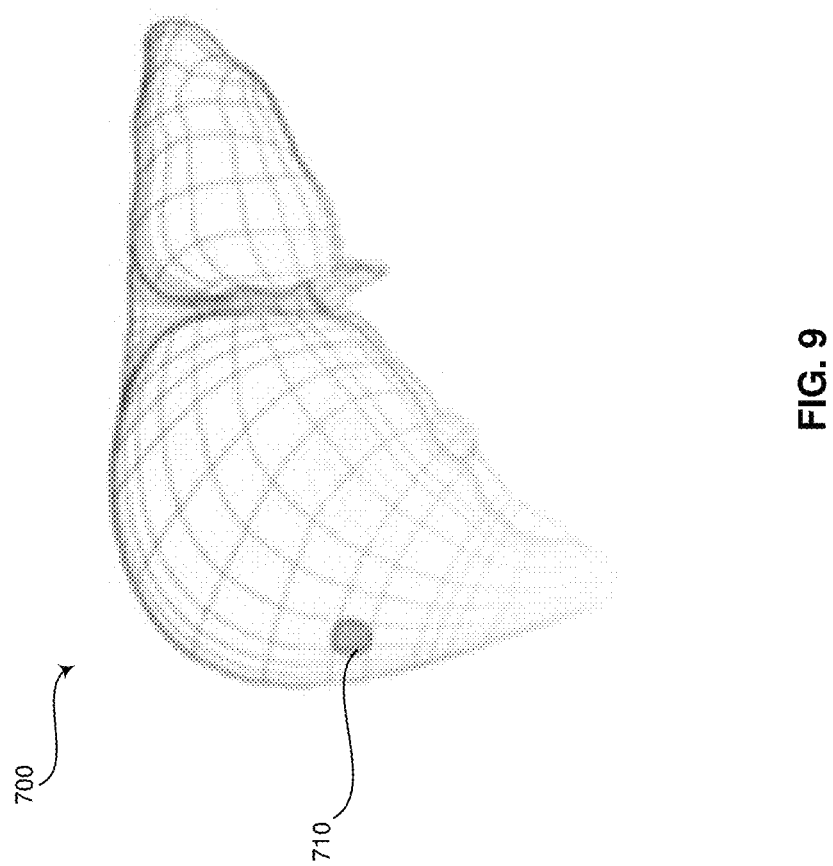
FIG. 9 is a perspective view of an exemplary patient-specific organ model having an exemplary contextual marker, in accordance with various embodiments.

FIG. 9 is a perspective view of an exemplary patient-specific organ model 700 having an exemplary contextual marker 710, in accordance with various embodiments. Referring to FIG. 9, the patient-specific organ model 700 comprises a contextual marker 710 that identifies the position of a structure or notation with respect to ultrasound image data of the organ. For example, the structure may be a lesion or any suitable structure. As another example, the notation may be comments, measurements, or other information added by an ultrasound operator during image acquisition or during subsequent review by a doctor, among other things. The contextual marker 710 and its position with reference to the patient-specific organ model 700 provide a three-dimensional context to the structure or notation in the ultrasound image data set. In various embodiments, the contextual marker 710 may be selected with the user input module 130 to retrieve the ultrasound image(s) 300 having the structure and/or notation for presentation at the display system 134.

Referring again to FIG. 1, the teaching engine 170 may comprise suitable logic, circuitry, interfaces and/or code that may be operable to train the neurons of the deep neural network(s) of the image registration module 150. For example, the teaching engine 170 may train the deep neural networks of the image registration module 150 using databases(s) of classified images. As an example, an image registration module 150 deep neural network may be trained by the teaching engine 170 with images of a particular organ to train the image registration module 150 with respect to the characteristics of the particular organ, such as the appearance of structure edges, the appearance of structure shapes based on the edges, the positions of the shapes relative to landmarks 310, 510 in the ultrasound image data 300, and the like. In certain embodiments, the organ may be a liver and the structural information may include information regarding the edges, shapes, and positions of a diaphragm, gallbladder, inferior vena cava, middle, liver-fat boundary, liver surface points, and/or the like. In various embodiments, the databases of training images may be stored in the archive 138 or any suitable data storage medium. In certain embodiments, the training engine 170 and/or training image databases may be external system(s) communicatively coupled via a wired or wireless connection to the ultrasound system 100.

Figure 10:
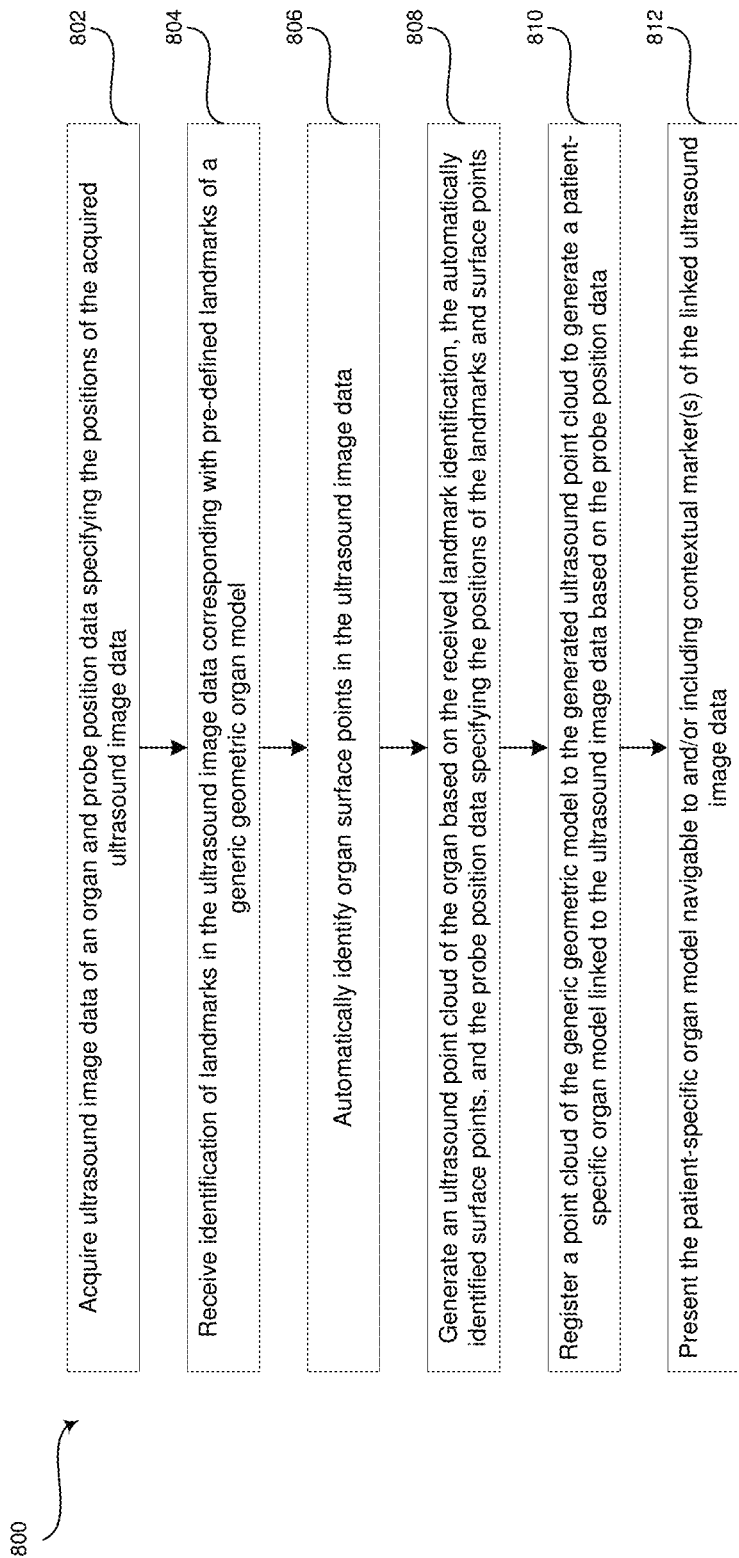
FIG. 10 is a flow chart illustrating exemplary steps that may be utilized for generating a patient-specific organ model from ultrasound image data, in accordance with exemplary embodiments.

FIG. 10 is a flow chart 800 illustrating exemplary steps 802-812 that may be utilized for generating a patient-specific organ model 700 from ultrasound image data, in accordance with exemplary embodiments. Referring to FIG. 10, there is shown a flow chart 800 comprising exemplary steps 802 through 812. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 802, an ultrasound system 100 may acquire ultrasound image data 300 of an organ and probe position data specifying the positions of the acquired ultrasound image data 300. For example, the ultrasound system 100 may acquire ultrasound image data 300 with an ultrasound probe 104 having a position sensing system 112. The ultrasound probe 104 may provide ultrasound image data corresponding with at least a substantial portion of an organ, such as a liver or any suitable organ. The position sensing system 112 may provide probe position data that is provided to a signal processor 132 of the ultrasound system 100. The signal processor 132 may associate the probe position data with the corresponding ultrasound image data acquired at each of the ultrasound probe positions.

At step 804, a signal processor 132 of the ultrasound system 100 may receive an identification of landmarks 310, 510 in the ultrasound image data 300 corresponding with pre-defined landmarks 210, 410 of a generic geometric organ model 200, 400. For example, a landmark identification module 140 of the signal processor 132 may receive the identification via a user input module 130 during acquisition of the ultrasound image data by an ultrasound operator. As another example, the landmark identification module 140 of the signal processor may receive the identification via the user input module 130 subsequent to the acquisition of the ultrasound image data during a review process by a doctor. The received landmarks 310, 510 identifications may correspond with pre-defined landmark 210, 410 positions in the generic geometric organ model 200, 400. For example, if the organ is a liver, the pre-defined landmarks may include midpoints and/or one or more of the most inferior, superior, lateral, medial, anterior, and/or posterior points, among other points, of the liver.

At step 806, the signal processor 132 may automatically identify organ surface points 505 in the ultrasound image data 300. For example, the landmark identification module 140 of the signal processor 132 may employ image detection and/or machine learning algorithms to identify points 505 along a surface of an imaged organ in the ultrasound image data 300. In various embodiments, the landmark identification module 140 may include deep neural network(s) made up of an input layer, output layer, and one or more hidden layers between the input and output layer. Each of the layers may perform a processing function before passing the processed ultrasound information to a subsequent layer for further processing.

At step 808, the signal processor 132 may generate an ultrasound point cloud 500 of the organ based on the received landmark identification, the automatically identified surface points, and the probe position data specifying the positions of the landmarks and surface points. For example, the landmark identification module 140 of the signal processor 132 may create the patient-specific ultrasound point cloud 500 by positioning the identified landmark and surface points 505, 510 based on the ultrasound probe position data received from the position sensing system 112.

At step 810, the signal processor 132 may register a point cloud 400 of the generic geometric model 200 to the generated ultrasound point cloud 500 to create a patient-specific organ model 700 linked to the ultrasound image data 300 based on the probe position data. For example, an image registration module 150 of the signal processor 132 may employ image registration techniques, such as landmark guided Coherent Point Drift (CPD) algorithms or any suitable image registration techniques, to deform the generic geometric model point cloud 400 to the patient-specific ultrasound point cloud 500 generated at step 808. The image registration module 150 may provide surfaces connecting the registered point clouds 600. In various embodiments, the surfaces added to the registered point cloud 600 may be post-processed to perform surface smoothing, texturing, and the like, resulting in the three-dimensional patient-specific organ model 700. In an exemplary embodiment, each position within the three-dimensional patient-specific organ model 700 may be linked to the acquired ultrasound image data based on the probe position data provided by the position sensing system 112. In a representative embodiment, ultrasound image data of the same patient acquired during subsequent examinations may be linked to the existing three-dimensional patient-specific organ model 700 based on the probe position data provided by the position sensing system 112. The generated patient-specific organ model 700 may be stored in archive 138 or any suitable data storage medium.

As an alternative to registering the generic geometric model point cloud 400 to the patient-specific ultrasound point cloud 500 as described in step 810, various embodiments may additionally and/or alternatively provide registering a mesh model with detailed node connectivity details corresponding with the generic geometric organ model 200 to the landmarks 310, 510 and surface points 505 identified in the acquired ultrasound images 300. For example, iterative closest point registration or any suitable mesh registration method may be applied to deform the mesh model of the generic geometric organ model 200 to match the patient specific landmarks 310, 510 and surface points 505.

At step 812, the signal processor 132 may present the patient-specific organ model 700 navigable to and/or including contextual marker(s) 710 from the linked ultrasound image data 300. For example, a patient-specific organ model context module 160 of the signal processor 132 may be configured to present the patient-specific organ model 700 at a display system 134 of the ultrasound system 100. In various embodiments, the patient-specific organ model 700 is navigable to retrieve and present ultrasound image data 300 corresponding with selectable positions in the patient-specific organ model 700. The patient-specific organ model 700 may provide a three-dimensional context to the two-dimensional ultrasound image being presented at the display system 134 by including contextual marker(s) 710 in the patient-specific organ model 700 illustrating the position of the displayed two-dimensional ultrasound image with respect to the organ. In certain embodiments, structure, notes, measurements, and other information marked in the two-dimensional ultrasound images by an ultrasound operator or doctor may appear in the patient-specific organ model 700 as one or more contextual markers 710. The contextual marker(s) 710 allow a viewer to determine where the identified structure, notes, measurements, or the like are located with respect to the organ. For example, the contextual marker 710 may identify a location of a lesion with respect to the patient-specific organ model 700.

In a representative embodiment, the patient-specific organ model context module 160 may be operable to perform volume or any suitable measurements of the patient-specific organ model 700 to determine, among other things, changes in size of the organ. In an exemplary embodiment, the patient-specific organ model 700 may be used to provide real-time navigation of a medical instrument, such as a needle or any suitable medical instrument, during a medical procedure, such as a biopsy or any suitable medical procedure. For example, the patient-specific organ model context module 160 may superimpose an icon corresponding with the medical instrument on to the patient-specific organ model 700 at a position based on a comparison of medical instrument position data compared to the probe position data associated with the patient-specific organ model 700. The position of the icon may be continuously updated based on received medical instrument position data.

Aspects of the present disclosure provide a method 800 and system 100 for generating a patient-specific organ model 700 from ultrasound image data 300. In accordance with various embodiments, the method 800 may comprise acquiring 802, by an ultrasound probe 104 having a position sensing system 112, ultrasound images 300 of an organ and probe position data corresponding with each of the ultrasound images 300. The method 800 may comprise receiving 804, by a processor 132, 140, identification of landmarks 310, 510 in one or more of the ultrasound images 300 corresponding with pre-defined landmarks 210, 410 of a generic geometric organ model 200, 400. The method 800 may comprise automatically identifying 806, by the processor 132, 140, surface points 505 of the organ in one or more of the ultrasound images 300. The method 800 may comprise generating 808, by the processor 132, 140, a patient-specific ultrasound point cloud 500 of the organ based on the received identification of the landmarks 310, 510, the automatically identified surface points of the organ 505, and the probe position data. The method 800 may comprise registering 810, by the processor 132, 150, a point cloud 400 of the generic geometric model 200 to the patient-specific ultrasound point cloud 500 to create a patient-specific organ model 700. The method 800 may comprise presenting 812 the patient-specific organ model 700 at a display system 134.

In an exemplary embodiment, locations within the patient-specific organ model 700 are linked to the ultrasound images 300 based on the probe position data. In certain embodiments, the patient-specific organ model 700 comprises a contextual marker 710 provided at one of the locations to visually identify information added to one of the ultrasound images 300 linked with the one of the locations in the patient-specific organ model 700. In a representative embodiment, the method 800 comprises presenting one or more of the ultrasound images 300 at the display system 134 in response to a selection of one of the locations within the patient-specific organ model 700. In various embodiments, the patient-specific organ model 700 comprises a contextual marker 710 identifying the selected one of the locations corresponding with the one or more of the ultrasound images 300 presented at the display system 134. In an exemplary embodiment, the point cloud 400 of the generic geometric model 200 is registered to the patient-specific ultrasound point cloud 500 based on landmark guided Coherent Point Drift algorithms. In certain embodiments, the surface points 505 of the organ are automatically identified by the processor 132, 140 based on machine-learning algorithms. In a representative embodiment, the method 800 comprises performing, by the processor 132, 160, a volume measurement of the patient-specific organ model 700.

Various embodiments provide a system 100 for generating a patient-specific organ model 700 from ultrasound image data 300. The system 100 may comprise an ultrasound probe 104 having a position sensing system 112, a user input module 130, a processor 132, 140, 150, 160, and a display system 134. The ultrasound probe 104 may be configured to acquire ultrasound images 300 of an organ. The position sensing system 112 may be configured to acquire probe position data corresponding with each of the ultrasound images 300. The user input module 130 may be operable to provide the processor 132, 140, 150, 160 with identification of landmarks 310, 510 in one or more of the ultrasound images 300 corresponding with pre-defined landmarks 210, 410 of a generic geometric organ model 200. The processor 132, 140, 150, 160 may be configured to automatically identify surface points 505 of the organ in one or more of the ultrasound images 300. The processor 132, 140, 150, 160 may be configured to generate a patient-specific ultrasound point cloud 500 of the organ based on the identification of the landmarks 310, 510 provided by the user input module 130, the automatically identified surface points 505 of the organ, and the probe position data. The processor 132, 140, 150, 160 may be configured to register a point cloud 400 of the generic geometric model 200 to the patient-specific ultrasound point cloud 500 to create a patient-specific organ model 700. The display system 134 may be configured to present the patient-specific organ model 700.

In a representative embodiment, locations within the patient-specific organ model 700 are linked to the ultrasound images 300 based on the probe position data. In an exemplary embodiment, the patient-specific organ model 700 comprises a contextual marker 710 provided at one of the locations to visually identify information added to one of the ultrasound images 300 linked with the one of the locations in the patient-specific organ model 700. In certain embodiments, one or more of the ultrasound images 300 is presented at the display system 134 in response to a selection of one of the locations within the patient-specific organ model 700 via the user input module 134. In various embodiments, the patient-specific organ model 700 comprises a contextual marker 710 identifying the selected one of the locations corresponding with the one or more of the ultrasound images 300 presented at the display system 134. In a representative embodiment, the processor 132, 140, 150, 160 is configured to perform a volume measurement of the patient-specific organ model 700. In an exemplary embodiment, the point cloud 400 of the generic geometric model 200 is registered to the patient-specific ultrasound point cloud 500 based on landmark guided Coherent Point Drift algorithms. In various embodiments, the surface points 505 of the organ are automatically identified by the processor 132, 140, 150, 160 based on machine-learning algorithms.

Certain embodiments provide a non-transitory computer readable medium having stored thereon, a computer program having at least one code section. The at least one code section is executable by a machine for causing the machine to perform steps. The steps 800 may include acquiring 802 ultrasound images 300 of an organ and probe position data corresponding with each of the ultrasound images 300. The steps 800 may include receiving 804 identification of landmarks 310, 510 in one or more of the ultrasound images 300 corresponding with pre-defined landmarks 210, 410 of a generic geometric organ model 200. The steps 800 may include automatically identifying 806 surface points 505 of the organ in one or more of the ultrasound images 300. The steps 800 may include generating 808 a patient-specific ultrasound point cloud 500 of the organ based on the received identification of the landmarks 310, 510, the automatically identified surface points 505 of the organ, and the probe position data. The steps 800 may include registering 810 a point cloud 400 of the generic geometric model 200 to the patient-specific ultrasound point cloud 500 to create a patient-specific organ model 700. The steps 800 may include presenting 812 the patient-specific organ model 700 at a display system 134.

In various embodiments, locations within the patient-specific organ model 700 are linked to the ultrasound images 300 based on the probe position data. In certain embodiments, the patient-specific organ model 700 comprises a contextual marker 710 provided at one of the locations to visually identify information added to one of the ultrasound images 300 linked with the one of the locations in the patient-specific organ model 700. In an exemplary embodiment, the steps 800 may include presenting one or more of the ultrasound images 300 at the display system 134 in response to a selection of one of the locations within the patient-specific organ model 700. In a representative embodiment, the patient-specific organ model 700 comprises a contextual marker 710 identifying the selected one of the locations corresponding with the one or more of the ultrasound images 300 presented at the display system 134.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein generating a patient-specific organ model from ultrasound image data.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   receiving, by a processor, ultrasound images of an organ and probe position data corresponding with each of the ultrasound images;
   receiving, by the processor, identification of landmarks in a first one or more of the ultrasound images corresponding with pre-defined landmarks of a generic geometric organ model;
   automatically identifying, by the processor, surface points of the organ in a second one or more of the ultrasound images;
   generating, by the processor, a patient-specific ultrasound point cloud of the organ based on the received identification of the landmarks, the automatically identified surface points of the organ, and the probe position data;
   registering, by the processor, a point cloud of the generic geometric model to the patient-specific ultrasound point cloud to create a patient-specific organ model; and
   presenting the patient-specific organ model at a display system.

2. The method of claim 1, comprising linking locations within the patient-specific organ model to the received ultrasound images of the organ based on the probe position data.

3. The method of claim 2, wherein the patient-specific organ model comprises a contextual marker provided at one of the locations to visually identify information added to one of the ultrasound images linked with the one of the locations in the patient-specific organ model.

4. The method of claim 2, comprising presenting at least one of the received ultrasound images of the organ at the display system in response to a selection of one of the locations within the patient-specific organ model, wherein the patient-specific organ model comprises a contextual marker identifying the selected one of the locations linked with the at least one of the received ultrasound images of the organ presented at the display system.

5. The method of claim 1, comprising acquiring, by an ultrasound probe having a position sensing system, the ultrasound images of the organ and probe position data corresponding with each of the ultrasound images.

6. The method of claim 1, wherein the point cloud of the generic geometric model is registered to the patient-specific ultrasound point cloud based on landmark guided Coherent Point Drift algorithms.

7. The method of claim 1, wherein the surface points of the organ are automatically identified by the processor based on machine-learning algorithms.

8. The method of claim 1, comprising performing, by the processor, a volume measurement of the patient-specific organ model.

9. A system comprising:
   a processor configured to:
      receive ultrasound images of an organ and probe position data corresponding with each of the ultrasound images;
      receive identification of landmarks in a first one or more of the ultrasound images corresponding with pre-defined landmarks of a generic geometric organ model;
      automatically identify surface points of the organ in a second one or more of the ultrasound images;
      generate a patient-specific ultrasound point cloud of the organ based on the identification of the landmarks, the automatically identified surface points of the organ, and the probe position data; and
      register a point cloud of the generic geometric model to the patient-specific ultrasound point cloud to create a patient-specific organ model; and
   a display system configured to present the patient-specific organ model.

10. The system of claim 9, wherein the processor is configured to link locations within the patient-specific organ model to the received ultrasound images of the organ based on the probe position data.

11. The system of claim 10, wherein the patient-specific organ model comprises a contextual marker provided at one of the locations to visually identify information added to one of the ultrasound images linked with the one of the locations in the patient-specific organ model.

12. The system of claim 10, wherein the processor is configured to receive a selection of one of the locations within the patient-specific organ model and, in response to the selection, cause at least one of the received ultrasound images of the organ to be presented at the display system, wherein the patient-specific organ model comprises a contextual marker identifying the selected one of the locations linked with the at least one of the received ultrasound images of the organ presented at the display system.

13. The system of claim 12, comprising:
- an ultrasound probe having a position sensing system, wherein the ultrasound probe is configured to acquire the ultrasound images of the organ, and wherein the position sensing system is configured to acquire the probe position data corresponding with each of the ultrasound images; and
- a user input device operable to provide the processor with the identification of the landmarks in the first one or more ultrasound images corresponding with the pre-defined landmarks of the generic geometric organ model.

14. The system of claim 9, wherein the processor is configured to perform a volume measurement of the patient-specific organ model.

15. The system of claim 9, wherein one or both of:
- the point cloud of the generic geometric model is registered to the patient-specific ultrasound point cloud based on landmark guided Coherent Point Drift algorithms, and
- the surface points of the organ are automatically identified by the processor based on machine-learning algorithms.

16. A non-transitory computer readable medium having stored thereon, a computer program having at least one code section, the at least one code section being executable by a machine for causing the machine to perform steps comprising:
- receiving ultrasound images of an organ and probe position data corresponding with each of the ultrasound images;
- receiving identification of landmarks in a first one or more of the ultrasound images corresponding with pre-defined landmarks of a generic geometric organ model;
- automatically identifying surface points of the organ in a second one or more of the ultrasound images;
- generating a patient-specific ultrasound point cloud of the organ based on the received identification of the landmarks, the automatically identified surface points of the organ, and the probe position data;
- registering a point cloud of the generic geometric model to the patient-specific ultrasound point cloud to create a patient-specific organ model; and
- presenting the patient-specific organ model at a display system.

17. The non-transitory computer readable medium of claim 16, wherein the steps comprise linking locations within the patient-specific organ model to the received ultrasound images of the organ based on the probe position data.

18. The non-transitory computer readable medium of claim 17, wherein the patient-specific organ model comprises a contextual marker provided at one of the locations to visually identify information added to one of the ultrasound images linked with the one of the locations in the patient-specific organ model.

19. The non-transitory computer readable medium of claim 17, wherein the steps comprise causing at least one of the received ultrasound images of the organ to be presented at the display system in response to a selection of one of the locations within the patient-specific organ model.

20. The non-transitory computer readable medium of claim 19, wherein the patient-specific organ model comprises a contextual marker identifying the selected one of the locations linked with the at least one of the received ultrasound images of the organ presented at the display system.

* * * * *